(12) United States Patent  
Weiss et al.

(10) Patent No.: US 9,274,070 B2  
(45) Date of Patent: Mar. 1, 2016

(54) SYSTEM AND PROCESS FOR MEASURING STRAIN IN MATERIALS AT HIGH SPATIAL RESOLUTION

(71) Applicant: APPFIVE, LLC, Tempe, AZ (US)

(72) Inventors: Jon Karl Weiss, Tempe, AZ (US);
Amith D. Darbal, Tempe, AZ (US);
Raman D. Narayan, Tempe, AZ (US);
Steven T. Kim, Tempe, AZ (US);
Stavros Nicolopoulos, Brussels (BE)

(73) Assignee: APPFIVE, LLC, Tempe, AZ (US)

( * ) Notice: Subject to any disclaimer, the term of this patent is extended or adjusted under 35 U.S.C. 154(b) by 0 days.

(21) Appl. No.: 14/383,713

(22) PCT Filed: Mar. 8, 2013

(86) PCT No.: PCT/US2013/029947
§ 371 (c)(1),
(2) Date: Sep. 8, 2014

(87) PCT Pub. No.: WO2012/134680
PCT Pub. Date: Sep. 12, 2013

(65) Prior Publication Data
US 2015/0076346 A1 Mar. 19, 2015

Related U.S. Application Data

(60) Provisional application No. 61/608,413, filed on Mar. 8, 2012.

(51) Int. Cl.
*H01J 37/26* (2006.01)
*G01N 23/225* (2006.01)
(Continued)

(52) U.S. Cl.
CPC ............. *G01N 23/2251* (2013.01); *G01N 3/02* (2013.01); *G01N 23/20058* (2013.01);
(Continued)

(58) Field of Classification Search
USPC .................. 250/306, 307, 308, 309, 310, 311
See application file for complete search history.

(56) References Cited

U.S. PATENT DOCUMENTS

| 7,235,784 B2 | 6/2007 | Taniguchi et al. |
| 2003/0006373 A1* | 1/2003 | Koguchi et al. ............... 250/311 |

(Continued)

FOREIGN PATENT DOCUMENTS

| JP | 2000065762 A | 3/2000 |
| JP | 2007173132 A | 7/2007 |

*Primary Examiner* — Nicole Ippolito
(74) *Attorney, Agent, or Firm* — Blue Fillament Law PLLC; Avery N. Goldstein

(57) ABSTRACT

A process for measuring strain is provided that includes placing a sample of a material into a TEM as a sample. The TEM is energized to create a small electron beam with an incident angle to the sample. Electrical signals are generated that control multiple beam deflection coils and image deflection coils of the TEM. The beam deflection control signals cause the angle of the incident beam to change in a cyclic time-dependent manner. A first diffraction pattern from the sample material that shows dynamical diffraction effects is observed and then one or more of the beam deflection coil control signals are adjusted to reduce the dynamical diffraction effects. One or more of the image deflection coil control signals are then adjusted to remove any motion of the diffraction pattern. A diffraction pattern is then collected from a strained area of the material after the adjusting step, and the strain is then determined from a numerical analysis of the strained diffraction pattern compared to a reference diffraction pattern from an unstained area of the material.

37 Claims, 2 Drawing Sheets

(51) Int. Cl.
*G01N 23/20* (2006.01)
*H01J 37/295* (2006.01)
*G01N 3/02* (2006.01)

(52) U.S. Cl.
CPC .............. *H01J 37/26* (2013.01); *H01J 37/261* (2013.01); *H01J 37/2955* (2013.01); *H01J 2237/15* (2013.01); *H01J 2237/2448* (2013.01); *H01J 2237/24585* (2013.01); *H01J 2237/2602* (2013.01); *H01J 2237/2802* (2013.01)

(56) References Cited

U.S. PATENT DOCUMENTS

2004/0061053 A1* 4/2004 Taniguchi ............... G01L 1/241
  250/310
2010/0246993 A1 9/2010 Rieger et al.
2011/0073757 A1 3/2011 Tanaka

* cited by examiner $$\begin{bmatrix} x' \\ y' \\ 1 \end{bmatrix} = A \begin{bmatrix} x \\ x \\ 1 \end{bmatrix} = \begin{bmatrix} a_{xx} & a_{xy} & t_x \\ a_{yx} & a_{yy} & t_y \\ 0 & 0 & 1 \end{bmatrix} \begin{bmatrix} x \\ y \\ 1 \end{bmatrix}$$

$$a_{xx} = s_x \cos\theta \quad a_{yy} = s_y \cos\theta$$

$$a_{xy} = s_y(\sin\alpha - \sin\theta) \quad a_{yx} = s_x \sin\theta$$

$$s_x = \frac{a'}{a} \quad s_y = \frac{b'}{b}$$

SYSTEM AND PROCESS FOR MEASURING STRAIN IN MATERIALS AT HIGH SPATIAL RESOLUTION

The application claims priority benefit of U.S. Provisional Application Ser. No. 61/608,413 filed 8 Mar. 2013; the contents of which are hereby incorporated by reference.

FIELD OF THE INVENTION

The invention in general relates to a system and process for electron microscopy to determine the local strain in materials, and in particular to precession electron diffraction and the generation of position-resolved strain distributions from samples subjected to electron microscopy.

BACKGROUND

Electron diffraction patterns offer the ability to measure the lattice parameters of crystalline materials. A small (<10 nanometer (nm)) focused electron probe can be produced by a transmission electron microscope ("TEM"), and the probe can be positioned in two dimensions to a precision of better than 1 nm. The probe is amenable to being moved quickly (<1 ms) to any position over a large (>1 µm) field of view. For electron-transparent samples, it is therefore possible to produce so-called nanobeam diffraction ("NBD") patterns from many discrete points in a sample.

NBD patterns have been used in the past to measure strain in crystalline samples. See, e.g., Koji Usuda et al., *Strain characterization in SOI and strained-Si on SGOI MOSFET channel using nano-beam electron diffraction (NBD)*, Materials Science and Engineering: B, Volumes 124-125, 5 Dec. 2005, Pages 143-147. The absolute strain is derived from the measured shift in position of one or more spots in the electron diffraction pattern from the strained crystal relative to the position of the same spots in the electron diffraction pattern from an unstrained crystal. Either manual measurement or semi-automated measurement using image/feature registration techniques have been used to measure the shift in the diffraction spots. But those methods suffer from some significant systematic errors that result from strong changes in the beam intensity distribution that are not due to strain (see the description of dynamical diffraction below). The precision required for some measurements, which can be less than 0.1% strain, is often not attainable with those methods.

The accuracy and precision of the strain measurement can be improved by fitting an entire diffraction pattern from a strained sample with another diffraction pattern from an unstrained sample that is distorted in directions corresponding to the strain vectors. By fitting the entire diffraction pattern instead of just individual spots, the accuracy and precision are improved over the measurement by including the physical constraint that the shifts of higher-index spots in one direction are linearly proportional to the shifts of their lower-index relatives. The stochastic uncertainly is also reduced by fitting all of the diffraction spots, as opposed to only measuring the limited number of spots whose intensity distribution is not changed too much by dynamical diffraction.

The main systematic errors in measuring spot positions from conventional NBD patterns, and therefore in calculating strain within a material, arise from the fact that the diffraction spot intensities and centers of mass are strongly affected by dynamical electron diffraction. A shift in center of mass of a diffraction spot leads to an error in measuring the spot shift, and the variation in spot intensities can lead to errors in fitting a complete diffraction pattern. The dynamical diffraction effect is strongly influenced by the relative beam/crystal orientation and by sample thickness. Relative orientation variations occur because of sample bending, which is common for thin TEM samples, while local variations in sample thickness are virtually unavoidable using common TEM sample preparation techniques.

Precession electron diffraction ("PED") has been used to reduce the negative effects of dynamical diffraction. See, e.g., R. Vincent, P. A. Midgley, *Double conical beam-rocking system for measurement of integrated electron diffraction intensities*, Ultramicroscopy, Volume 53, Issue 3, March 1994, Pages 271-282. In PED, the incident electron beam is precessed at a relatively high frequency (10-1000 Hz) through a small (0.2-5 degrees) angle. This precession reduces the visible effects of dynamical diffraction, so that the diffraction patterns are influenced minimally by variations in sample thickness and bending. Additionally, many additional higher-order reflections appear, which are more sensitive to strain than the lower-order reflections, further enhancing the precision of the strain measurement.

Thus, there exists a need for a process for measuring strain in materials with improved precision. There further exists a need for performing such measurements with high spatial resolution to allow other details of a sampled field to be correlated with strain values derived from the same sample area.

SUMMARY OF THE INVENTION

A process for measuring strain is provided that includes placing a sample of a material into a TEM as a sample. The TEM is energized to create a small electron beam with an incident angle to the sample. Electrical signals are generated that control multiple beam deflection coils and image deflection coils of the TEM. The beam deflection control signals cause the angle of the incident beam to change in a cyclic time-dependent manner. A first diffraction pattern from the sample material that shows dynamical diffraction effects is observed and then one or more of the beam deflection coil control signals are adjusted to reduce the dynamical diffraction effects. One or more of the image deflection coil control signals are then adjusted to remove any motion of the diffraction pattern. A diffraction pattern is then collected from a strained area of the material after the adjusting step, and the strain is then determined from a numerical analysis of the strained diffraction pattern compared to a reference diffraction pattern from an unstrained area of the material.

A system for measuring strain in a material includes a transmission electron microscope having beam deflection coils, image deflection coils, and a stage for receiving a sample of the material, and generating an electron beam upon being energized, the electron beam having an incident angle to the sample. A precession device generates electrical signals that control the beam deflection coils and image deflection coils. Software that controls the deflection coil control signals is also used to collect diffraction patterns from the sample, which are used by the software to determine the strain in the material.

DETAILED DESCRIPTION OF THE INVENTION

Figure 1:
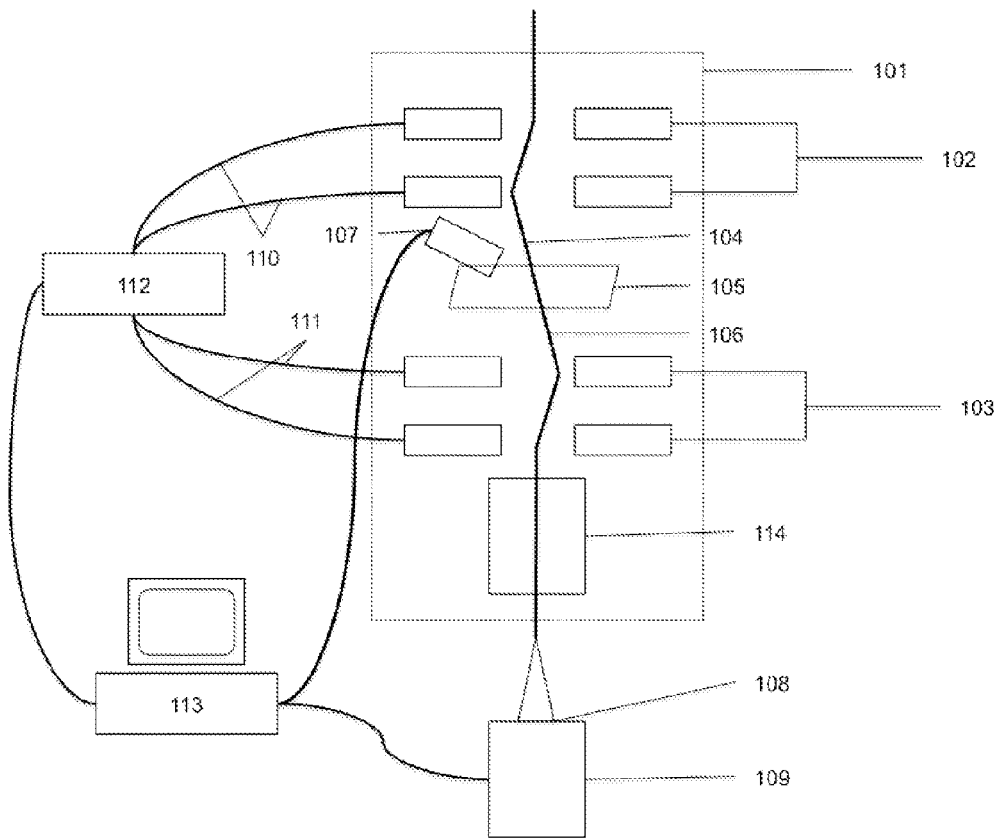
FIG. 1 is a diagram showing the major components of the present invention, along with a ray path of the electrons as they pass through the device.

The present invention has utility as a system and a process of performing PED in TEM. In one embodiment of the present invention, a TEM with an accelerating voltage between 20 kV and 1.5 MV is fitted with a device (the "Precession Device") that applies signals to the TEM that produce a time-dependent change in the angle of the incident electron beam. The Precession Device also applies signals to the TEM to stop the motion of the diffraction patterns that is induced by the change of angle of the incident electron beam. In specific embodiments, the incident electron beam is a small diameter probe that produces NBD patterns and raster scanned ("STEM") images. The TEM is also fitted in specific embodiments with a camera (the "Camera") to record TEM images and/or diffraction patterns. A computer, through software running on the computer (the "Software"), controls various operational aspects of the TEM, the Precession Device, and the Camera. The Software acquires PED patterns using the Camera, and can cause the position of the electron beam on the sample to change in a controlled manner.

PED patterns from a TEM sample are acquired using the Software from areas of unknown strain ("Unknown Pattern"). A PED pattern ("Reference Pattern") is either acquired using the Software from a TEM sample of known strain, or is calculated using the Software from a kinematical or dynamical diffraction theoretical model. It should be appreciated that calculated kinematical patterns are computationally more tractable than dynamical patterns, and also that diffraction patterns acquired with precession are a good representation of kinematical patterns, even for thicker samples. The Reference Pattern is acquired or calculated from a sample with the same crystalline structure and the same relative electron beam/sample orientation as from the Unknown Pattern. The Software uses a numerical image warping algorithm (see for example Wolberg, G. (1990), *Digital Image Warping*, IEEE Computer Society Press) to create a distorted version ("Distorted Pattern") of either the Reference Pattern or the Unknown Pattern, leaving the other pattern ("Undistorted Pattern") undistorted. The distortion will minimally include normal expansion or contraction and shear distortion in one or more directions in addition to rotation and translation. The magnitude of each distortion is described by a Distortion Coefficient. The Software determines the set of Distortion Coefficients that produces the best match of the Distorted Pattern to the Undistorted Pattern. From the Distortion Coefficients that produce the best match, the Software calculates the value of the unknown strain relative to the known strain.

The present invention also has application in instances when the Software acquires Unknown Patterns from arrays of positions on the sample. Each of the Unknown Patterns is processed as described above, and the calculated strains are assembled in the Software as one- or two-dimensional strain distributions.

According to the present invention, a TEM is also in certain embodiments fitted with an energy-dispersive X-ray ("EDX") detector that detects X-rays coming from the sample in the area illuminated by the electron beam and/or an electron energy loss spectroscopy ("EELS") detector which determines the energy losses of the electrons that have gone through the illuminated area of the sample. The Software or other software acquires spectra from the EDX and EELS detectors from the same positions as the PED patterns, and can derive compositional information that is spatially registered with strain information for the TEM sample.

With reference to FIG. 1, a TEM 101 has an attached Precession Device 112 and Camera 109. The Precession Device 112 generates beam coil control electrical signals 110 that control the beam deflection coils 102, which in turn control the angle and the position of the electron beam or probe 104 incident on the sample 105. The Precession Device 112 also generates image deflection coil electrical signals 111 that control the image deflection coils 103, which in turn compensate for the effect of the incident beam tilt and shift on the transmitted beam 106. The Precession Device generates incident beam tilts according to various cyclic tilt protocols, at characteristic tilt angles of typically 0.1 to 2 degrees, and at frequencies of typically 10-1000 Hz. The image compensation signals 111 are adjusted so the diffraction pattern 108 remains at a fixed position while the incident beam is tilted according to its defined protocol.

A sample 105 is placed in a TEM as a specimen to be measured and is tilted to an orientation such that a diffraction pattern 108 is observed containing diffraction spots corresponding to the lattice directions in which the strain is to be measured. It is appreciated that the specific orientation of the sample 105 is immaterial to the inventive process. The characteristic tilt angle of the tilt protocol is adjusted so that minimal dynamical diffraction effects are observed. This minimal dynamical diffraction effect adjustment can be observed by changing the position of the incident electron beam, and when dynamical diffraction effects are minimal, there will be only minor changes in the observed diffraction patterns as the incident beam is moved. The electron beam 104 is then positioned on an area of the sample 105 of unknown strain, and one or more Unknown Patterns are acquired from the Camera 109 and are stored using the Software. The frequency of the tilt protocol is set such that the tilt protocol cycles an integral number of times during the Camera exposure. In one embodiment, the electron beam 104 is positioned on an area of the sample 105 of known (ideally zero) strain, and one or more Reference Patterns are acquired from the Camera 109 and are stored using the Software. In another embodiment, a Reference Pattern is calculated using the Software or using other software. In yet another embodiment, a Reference Pattern is recalled from a database of electron diffraction patterns using the Software. It is appreciated that additional spatial information can be obtained from a sample 105 through collection of TEM camera images or STEM images in order to locate specific areas for measuring strain. It should also be appreciated that a representative diffractogram is also readily obtained through Fourier transform of a TEM or STEM lattice image of the sample 105.

In some embodiments to the present invention, the sample 105 is held within a straining TEM specimen holder or anvil holder to induce dynamic strain or deformation of a sample with patterns collected as a function of forces applied to the sample 105. It is appreciated that such holders are also available with thermal and tilt control of the sample 105.

Figure 2:
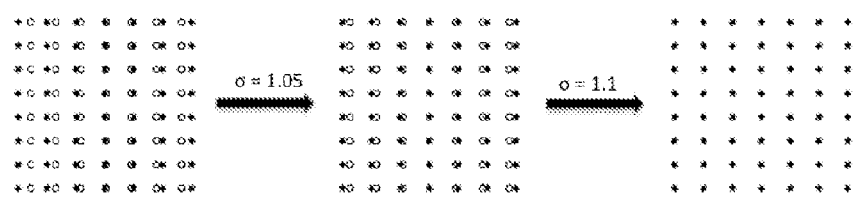
FIG. 2 is a depiction of the variation of the distortion parameter σ of the Distorted Pattern (open circles) that leads to a best match with the Undistorted Pattern (solid circles).
Figure 3:
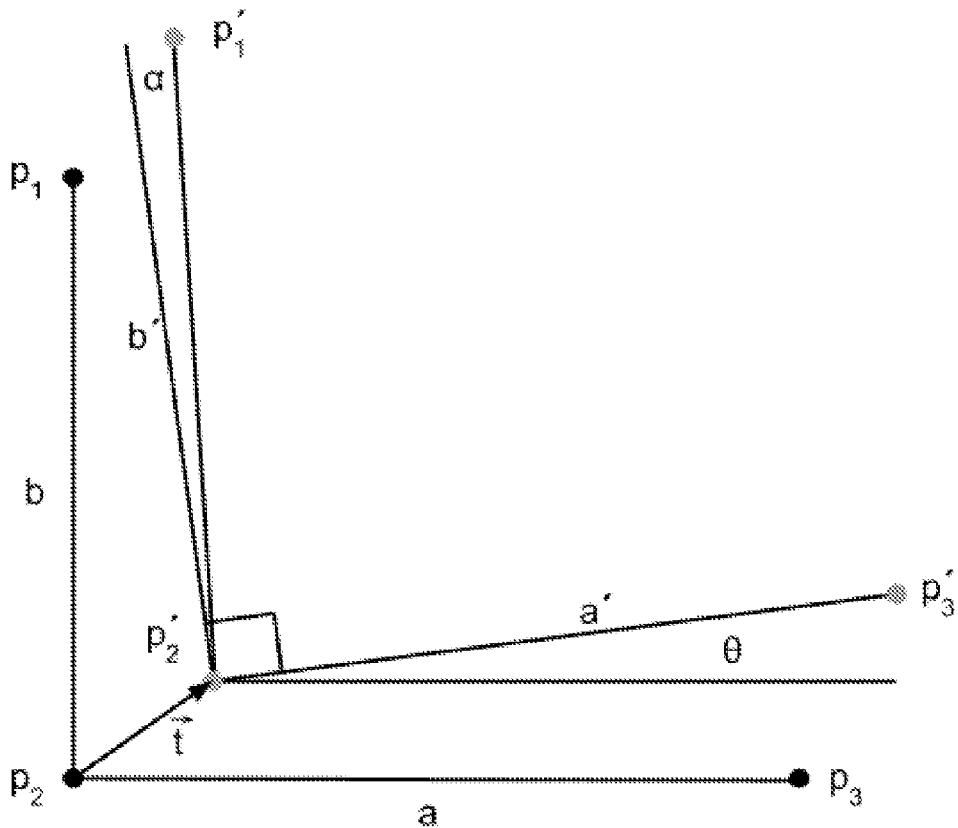
FIG. 3 is a depiction of the geometry of the affine transformation, along with the equations for the affine transformation and the relationship of the affine coefficients to the geometry.

One of either the Unknown Pattern or the Reference Pattern is numerically distorted by the Software in one or more directions with normal, shear, rotational and translational distortions. In one embodiment, the Distorted Pattern is distorted using an affine transformation of all pixels of the image, where the coefficients of the affine transformation are the Distortion Coefficients. Such a distortion can lead to some corresponding distortion of the shape of the diffraction spots. In another embodiment, each diffraction spot of the Distorted Pattern is individually extracted and translated by a vector calculated from an affine transformation and distortion coefficients are the coefficients of the affine transformation. Such a distortion will maintain the shape of the diffraction spots. FIG. 2 shows an example of such a distortion, where the affine transformation includes only a scale factor $\sigma$ in the x-direction. FIG. 3 shows the geometry and the functional form of the affine transformation. The normal strain components $\epsilon_{xx}$ and $\epsilon_{yy}$ are equal to $1/s_x$ and $1/s_y$, respectively, in the case that the Reference Pattern is distorted. The Distortion Coefficients (in this case the affine coefficients) are adjusted by the Software to produce a best match of the Distorted Pattern to the Undistorted Pattern. In specific embodiments, the best match is determined by Levenberg-Marquardt non-linear fitting, non-linear least squares regression, or by Gauss-Newton or other known regression algorithms. In still other embodiments, the best match is determined by maximizing the image cross correlation coefficient using a Quasi-Newton, other linear optimization algorithm, or simplex algorithm that varies the Distortion Coefficients.

It is appreciated that in other inventive aspects, the Software controls the position of the incident beam on the sample. Various patterns of incident beam positions are produced on the sample, including but not limited to multiple points along a curve, and two-dimensional grids of points within an area. At each position of the incident beam, the Software acquires and stores an Unknown Pattern from that position of the sample. A Measured Strain is calculated from each of the Unknown Patterns using the Fitting Algorithm, and the Software constructs a spatial distribution of strain (a "Strain Distribution"). It is appreciated that the diffraction pattern used for comparison can be a measured pattern, a calculated pattern, a library reference, or a combination thereof. A library of reference patterns is readily assembled by a standards generating facility or through contribution of patterns by a community of users.

Repetition of the inventive process is also used to generate a spatial map of the strain distributions across the sample through collection of diffraction patterns from different regions of the sample. Such topographical strain mapping is amenable to overlaying with spatially correlated chemical compositional information derived from the EDX and/or EELS detectors, or structural features obtained from TEM or STEM images, or a combination thereof.

It is appreciated that in other inventive aspects, an energy-dispersive X-ray detector 107 and/or EELS detector 114 is also mounted on the TEM. The Software acquires X-ray spectra from the EDX detector or EELS data from the EELS detector. Optionally, the EDX or EELS data is collected at the same position on the sample where the Software acquires PED patterns from the Camera. The Software analyzes the additional EDX or EELS data to determine the local elemental composition of the sample at the location of the incident beam, in addition to the measured strain at that location.

It is appreciated that in other inventive aspects, an energy-dispersive X-ray detector 107 and/or EELS detector 114 is also mounted on the TEM, and the Software positions the incident electron beam in patterns as described above. At each position of the incident beam, the Software acquires and stores an Unknown Pattern and an X-ray spectrum and/or EELS spectrum from that position of the sample. A Measured Strain is calculated from each of the Unknown Patterns using the Fitting Algorithm, and an elemental composition is calculated from each of the X-ray spectra and/or EELS spectra. The Software constructs a Strain Distribution, and also spatially registered elemental composition distributions ("Composition Distributions").

In certain embodiments of the present invention where an EELS detector is present, a process is provided in which at each position of the incident beam, the Software acquires and stores an Unknown Pattern and an X-ray spectrum and/or EELS spectrum from that position of the sample. A Measured Strain is calculated from each of the Unknown Patterns and an elemental composition is calculated from each of the X-ray spectra and/or EELS spectra. Such X-ray and EELS spectra may be acquired with any precession angle from 0 degrees (no precession) up to a specific precession angle (up to about 2 degrees) where the X-ray and EELS signal may be enhanced. (S. Estrade' et al., EELS signal enhancement by means of beam precession in the TEM, Ultramicroscopy (2012)). In addition to the compositional information in the EELS spectra, strain may affect the intensity, shape, or position of features in the EELS spectra. If these changes are correlated with the strain measured from the diffraction patterns, the features in the EELS spectra may be used as another measure of the strain in the sample.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for measuring strain in crystalline materials comprising:
    placing a sample of a material into a transmission electron microscope as a specimen; and
    energizing the transmission electron microscope to create an electron beam with an incident angle to the material; and
    generating electrical beam deflection coil control signals that control a plurality of beam deflection coils of the transmission electron microscope; and
    generating electrical image deflection coil control signals that control a plurality of image deflection coils of the transmission electron microscope;
    viewing a first diffraction pattern from the material with dynamical diffraction effects;
    adjusting at least one of the beam deflection coil control signals to reduce the dynamical diffraction effects;
    adjusting at least one of the image deflection coil control signals to stop the motion of the diffraction pattern induced by the beam deflection coil control signals;
    collecting after the last adjusting step a second diffraction pattern from an area of the material with known strain;
    collecting a third diffraction pattern from an area of the material with unknown strain.

2. The process of claim 1 wherein the beam deflection coil control signals modify the incident angle between 0.1 and 2 degrees.

3. The process of claim 1 wherein the beam deflection coil control signals change the beam incident angle in a cyclic time-dependent manner at a frequency of between 10-1000 Hz.

4. The process of claim 1 wherein the dynamical diffraction effect is observed by changing the position of the beam and is minimized when only minor changes are noted in the first diffraction pattern as the incident beam position is changed.

5. The process of claim 1 wherein the second diffraction pattern is collected with a camera.

6. The process of claim 1 wherein the second diffraction pattern is calculated using kinematical electron diffraction theory.

7. The process of claim 1 wherein the second diffraction pattern is recovered from a stored file.

8. The process of claim 1 further comprising collecting a third diffraction pattern with a camera.

9. The process of claim 1 further comprising collecting a third diffraction pattern with a camera and using an image warping algorithm with one or more distortion coefficients to create a distorted pattern of either the second or third diffraction pattern, and leaving the other diffraction pattern undistorted.

10. The process of claim 1 further comprising collecting a third diffraction pattern with a camera and using an image warping algorithm with one or more distortion coefficients to create a distorted pattern of either the second or third diffraction pattern, and leaving the other diffraction pattern undistorted wherein the image warping algorithm is an affine transformation and the distortion coefficients are the coefficients of the affine transformation.

11. The process of claim 10 further comprising measuring the quality of the match between the distorted pattern and the undistorted pattern.

12. The process of claim 11 further comprising finding the distortion coefficients that produce the highest quality match between the distorted pattern and the undistorted pattern.

13. The process of claim 12 further comprising determining the measured strain in one or more directions in the sample from the values of the distortion coefficients.

14. The process of claim 13 wherein the algorithm for finding the best match is a nonlinear least squares fitting algorithm to fit the distorted pattern to the undistorted pattern, where the fitting parameters for the algorithm are the distortion coefficients.

15. The process of claim 13 wherein the quality of the match is defined by the image cross correlation coefficient between the undistorted pattern and the distorted pattern, and the algorithm for finding the highest quality match is a linear optimization algorithm to find the maximum value of the cross correlation coefficient, where the input values for the optimization algorithm are the distortion coefficients.

16. The process of claim 14 further comprising collecting a plurality of third diffraction patterns from different positions on the sample.

17. The process of claim 16 further comprising measuring the strain from the diffraction patterns at each position on the sample.

18. The process of claim 17 further comprising creating one or more maps of the strain distributions across the sample.

19. The process of claim 14 further comprising measuring a chemical composition of the material.

20. The process of claim 19 wherein measuring the chemical composition of the material occurs at the position where the third diffraction pattern was acquired.

21. The process of claim 19 wherein measuring the chemical composition of the material is by energy dispersive X-ray spectroscopy and/or electron energy loss spectroscopy.

22. The process of claim 18 further comprising measuring the chemical composition of the material at each position where a diffraction pattern was acquired.

23. The process of claim 22 wherein measuring the chemical composition of the material is by energy dispersive X-ray spectroscopy and/or electron energy loss spectroscopy.

24. The process of claim 23 further comprising creating one or more maps of the chemical composition distribution across the sample.

25. The process of claim 15 further comprising collecting a plurality of third diffraction patterns from different positions on the sample.

26. The process of claim 25 further comprising measuring the strain from the diffraction patterns at each position on the sample.

27. The process of claim 26 further comprising creating one or more maps of the strain distributions across the sample.

28. The process of claim 15 further comprising measuring a chemical composition of the material.

29. The process of claim 28 wherein measuring the chemical composition of the material occurs at the position where the third diffraction pattern was acquired.

30. The process of claim 28 wherein measuring the chemical composition of the material is by energy dispersive X-ray spectroscopy and/or electron energy loss spectroscopy.

31. The process of claim 27 further comprising measuring the chemical composition of the material at each position where a diffraction pattern was acquired.

32. The process of claim 31 wherein measuring the chemical composition of the material is by energy dispersive X-ray spectroscopy and/or electron energy loss spectroscopy.

33. The process of claim 32 further comprising creating one or more maps of the chemical composition distribution across the sample.

34. A system for measuring strain in a material comprising:
a transmission electron microscope having beam deflection coils and image deflection coils, a stage for receiving a sample of the material, and generating an electron beam upon being energized, the electron beam having an incident angle to the sample; and
a precession device generating electrical beam deflection coil control signals that control the beam deflection coils and electrical image deflection coil control signals that control the image deflection coils;
software for controlling the beam deflection coil control signals and the image deflection coil control signals to collect a set of diffraction patterns from the sample, where the software analyzes a first diffraction pattern from the set of diffraction patterns with dynamical diffraction effects, and in response to the analysis the software:
adjusts at least one of the beam deflection coil control signals to reduce the dynamical diffraction effects,
adjusts at least one of the image deflection coil control signals to stop the motion of the first diffraction pattern induced by the beam deflection coil control signals,
collects a second diffraction pattern from the set of diffraction patterns from an area of the material with known strain,
collects a third diffraction pattern from the set of diffraction patterns from an area of the material with unknown strain; and
wherein the software constructs a strain distribution and spatially registered elemental composition distributions based on the analysis in order to determine the strain in the material.

35. The system of claim 34 further comprising a camera positioned for collecting the diffraction patterns from the material.

36. The system of claim 34 wherein the incident angle of the beam is changed by the precession device between 0.1 and 2 degrees.

37. The system of claim 34 wherein the incident angle is changed in a cyclic time-dependent manner with a cyclic frequency of 10-1000 Hz.

* * * * *